(12) United States Patent
Pourrat et al.

(10) Patent No.: US 6,270,773 B1
(45) Date of Patent: Aug. 7, 2001

(54) PROCESS FOR STABILIZING VEGETABLE PLANTS

(75) Inventors: Aimée Gaillard Pourrat; Henri Pourrat, both of Clermont Ferrand (FR)

(73) Assignee: Gattefosse, S.A. (FR)

( * ) Notice: Subject to any disclaimer, the term of this patent is extended or adjusted under 35 U.S.C. 154(b) by 0 days.

(21) Appl. No.: 08/271,571

(22) Filed: Jul. 7, 1994

Related U.S. Application Data

(63) Continuation of application No. 08/032,456, filed on Mar. 17, 1993, now abandoned, which is a continuation of application No. 07/736,040, filed on Jul. 25, 1991, now abandoned.

(30) Foreign Application Priority Data

Aug. 30, 1990 (FR) .................................................. 90 10159

(51) Int. Cl.⁷ .................................................. A61K 35/78
(52) U.S. Cl. .......................................................... 424/195.1
(58) Field of Search .................... 424/195.1; 426/419, 426/443, 455, 465, 615

(56) References Cited

U.S. PATENT DOCUMENTS

| 4,520,574 | * | 6/1985 | Sugisawa | 34/5 |
| 4,614,660 | * | 9/1986 | Weibyg | 426/461 |
| 4,681,770 | * | 7/1987 | Palmer | 426/615 |
| 4,832,969 | * | 5/1989 | Lioutas | 426/270 |

FOREIGN PATENT DOCUMENTS

2553873 * 10/1983 (FR) .

OTHER PUBLICATIONS

Derwent Central Patents Index, Basic Abstracts Journal, 8503, Accession No. 016069/03, Derwent Publications Ltd., GB; & JP–A–59 213 356 (Mitsui Toatsu Chem. Inc.) Mar. 12, 1984.

Derwent Central Patents Index, Basic Abstracts Journal, 8705, Accession No. 033273/05, Derwent Publications Ltd., GB & JP–A–61 289 855 (Morinaga & Co., Ltd) Dec. 19, 1986.

Derwent Central Patents Index, Basic Abstracts Journal, Sec. C, AGDOC Accession No. 21025K/09, Derwent Publ., Ltd., & JP–A–58 010 502 No Date Avail.

Derwent Central Patents Index, Basic Abstracts Journal, Sec. B, Acc. No. 083142/14, Derwent Publ., Ltd., & HU–A–34 219(Richter Gedeon Vegy.) Feb. 28, 1985.

* cited by examiner

*Primary Examiner*—Ralph Gitomer
(74) *Attorney, Agent, or Firm*—Wall, Marjama & Bilinski

(57) ABSTRACT

A process for preserving desired characteristics of vegetable plants for cosmetic, condimental, aromatic or food use is described which includes rehydrating harvested vegetable to nearly the water content of freshly harvested plants and then exposing them to microwave radiation to rapidly heat them to the denaturation temperature of the specific enzyme contained in the harvested plants.

5 Claims, No Drawings

PROCESS FOR STABILIZING VEGETABLE PLANTS

This is a continuation of application Ser. No. 08/032,456 filed on Mar. 17, 1993 now abandoned, which is a continuation of Ser. No. 07/736,040 filed Jul. 25, 1991, now abandoned.

The invention relates to a novel process for stabilising vegetable plants (designated hereinafter "plants"), such as in particular plants for medical, cosmetic, condimental, aromatic or food use.

BACKGROUND OF THE INVENTION

As is known, plants exhibit their optimal qualities at the time they are harvested. In contrast, these qualities deteriorate very rapidly. It is important therefore to "stabilise" them in order to try to preserve as much as possible the essential and desired component of these properties.

As is known, the stabilisation of fresh plants is a process which aims to preserve all the initial properties of these products, from the point of view of the therapeutic active ingredients (alkaloids, trace elements, vitamins, essential oils, polyphenols and the like), as well as other properties such as taste, colour and odour.

Most generally, in order to stabilise plants, they are air-dried. Although very widespread, this technique exhibits numerous disadvantages essentially related to the slowness of the procedure which leads to degradation, decoloration and deodorisation. All the processes for stabilising plants known hitherto aim to inactivate the enzymes which they contain. As is known, in practice, the denaturation of enzymes is obtained at a temperature which is specific for each enzyme, most often at temperatures between 70 and 90° C. Because of the poor thermal conductivity of plant tissues, some parts close to the surface heat up considerably whereas the temperature of the internal zones increases slowly. This is particularly distinct in the case of thick and ligneous organs.

In order to stabilise plants, that is to say annihilate the enzymes, processes which require the use of moist heat, water vapour, or even alcohol vapour, in particular ethanol, have hitherto essentially been used. Dry heat is hardly used because, as the temperature rise is slow, the enzymes unfortunately express their activity well before being destroyed.

The use of ultrahigh frequency currents on fresh or withered plants or for drying oleaginous seeds, for example of sunflower plants, in particular in order to improve the hulling of these seeds has already been proposed. These techniques have not been developed, probably because of their high cost as they require extremely long durations of treatment and have proved useful only for the treatment of seeds and not of plants.

SUMMARY OF THE INVENTION

The invention palliates these disadvantages. It relates to a process for stabilising vegetable plants without degrading their therapeutic active ingredients and while preserving their taste and their odour, which could not be economically and effectively achieved until now.

The process of the invention is carried out on uncut plant portions - that is whole fruit, aerial parts, leaves, roots and the like that have not been further cut.

This process for stabilising vegetable plants is characterised in that it consists in:

firstly, rehydrating the fresh plants in order to bring their water content close to the initial water content of the freshly harvested plant;

then subjecting this rehydrated plant to an ultrahigh frequency treatment until achieving in the plant a temperature at least equal to the denaturation temperature of the enzymes contained in this plant.

In other words, the invention consists firstly in rehydrating fresh plants in order to bring their free water content (which is known to represent about 75 to 90% of the water contained in a plant), close to their initial content, and then subjecting this superficially rehydrated plant to an ultrahigh frequency treatment until a temperature, at least equal to the denaturation temperature of the specific enzymes contained in this plant, is achieved. Thus, by virtue of the superficial rehydration, these plants have a high free water content which is known to exhibit very high dielectric losses, whereas the essential constituents of the tissue (cellulose and lignin) have only small dielectric losses, but nevertheless do not prevent the passage of ultrahigh frequency currents. Thus, following superficial rehydration, a rapid and homogeneous rise in temperature, which annihilates enzymatic activity without modifying other properties or denaturing other desired constituents, is produced during subsequent exposure to ultrahigh frequency radiation.

The process according to the invention makes it possible to selectively inactivate the enzymes contained in plants, in fresh plants in particular, while paying great attention to the therapeutic active ingredients contained in these plants.

As is known, "ultrahigh frequencies" also sometimes called U.H.F. waves designate electromagnetic waves whose wavelength is of the order of the centimeter. In industry, generators of these waves are magnetrons, or even klystrons.

Advantageously, in practice:

fresh plants are used in the procedure, that is to say plants which have lost at most a third of their initial free water and therefore may thus be rapidly rehydrated, that is to say in a few minutes;

the rehydration phase consists in covering the plant with at least a thin film of water in order, as already stated, to bring the water content of the plant close to its initial content, in particular of the order of 95% of this initial content; it has been observed that a rehydration level above 95% is difficult to achieve and does not allow a substantial improvement to be obtained;

rehydration is carried out at room temperature by immersing the plant in water, or even by spraying and then draining, followed optionally by shaking in order to eliminate excess surface water which may unnecessarily consume energy during subsequent ultrahigh frequency treatment;

the ultrahigh frequency treatment is combined with infrared heating and may be completed by natural drying, in particular at room temperature and in a ventilated atmosphere.

The characteristic phase of superficial external rehydration makes it possible to re-establish the passage between surface water and intracellular water, which is stirred by the ultrahigh frequency treatment. It is therefore important for the water content to be sufficient in order to obtain homogeneous dielectric losses in the whole volume of the plant to be treated, but, as already stated, it is unnecessary for this surface water to be in excess.

As a result, during subsequent ultrahigh frequency treatment, internal heating of the plant is greater by a few degrees than that of the external part. This results in the migration of water from the internal zones towards the external zones which becomes all the greater as the viscosity of the water decreases with the rise in temperature. This phenomenon facilitates the removal of a larger proportion of water, which enhances desiccation of the plant.

The ultrahigh frequency treatment is carried out in a known manner, for example by means of an oven equipped with several magnetrons or klystrons in order to obtain a better distribution, a better penetration and a better homogeneity of the ultrahigh frequency currents. It is important that the emission of waves is homogeneous. The frequencies of the magnetrons are chosen within the bands which are authorised for industrial use. Band B (2450 MHz) is preferably used. Optionally, band A, of 915 MHz, may also be used.

In a variant, the ultrahigh frequency treatment is combined with an infrared treatment which has the effect of facilitating a rise in the temperature of the water. The duration of treatment varies from one plant to another, depending on the nature of the enzymes contained in the plant, and on the proportion of ligneous tissue and the volume and nature of the plants (leaves, roots and the like) to be treated. The temperature is monitored by any suitable means, in particular by means of a heat probe placed in the centre of the material to be treated. As already stated, it is necessary to reach the denaturation temperature of the catalytic effect of the enzyme specific to each plant which is known to the specialist or which may easily be monitored by him using simple preliminary tests.

After this ultrahigh frequency treatment, the treated material may optionally be subjected to a drying procedure in order to bring the water content to that of the bound water. This additional drying may be carried out by natural means, in a particular at room temperature or in a ventilated atmosphere or even using ultrahigh frequencies in order to homogenise the drying, in particular when the additional cost of this step does not constitute an economic handicap for the plants concerned.

When all the free water, or most of it, has disappeared, heating of the treated plant is stopped so that the other desired constituents are not affected.

DETAILED DESCRIPTION OF A PREFERRED EMBODIMENT

In practice, the process according to the invention is carried out in the following manner.

The desired parts of the plant are harvested (aerial part, leaves, roots and the like).

The plants to be treated, still fresh, that is to say containing at least two-thirds of their initial water, are soaked by immersion at room temperature for a few minutes and then drained. They are then placed on racks made of low-loss dielectric material. The rack with its load is then introduced by a belt or by any other equivalent means into an ultrahigh frequency oven which is then closed. It is important that this oven is made ultrahigh frequency radiation-tight, for example by means of metal gaskets fixed to the open edge of the cavity. The oven comprises security mechanisms and side vents conform with the required standards. The exposure time is determined by preliminary tests depending on the denaturation temperature of the specific enzymes of the plant concerned. Commercial magnetrons (for example a sequence of 2 KW magnetrons in series), in particular with a forced-air cooling system and a system for mixing the waves emitted are used as magnetrons. Advantageously, the oven is ventilated in order to remove the water vapour formed. Homogeneity of the medium is provided by means of a buckled disc driven by a forward to backward movement. As already stated, the lower part of the oven may optionally be equipped with heating resistors or infrared lamps in order to combine ultrahigh frequency heating with conductive heating.

The racks are then taken out of the oven and drying is completed using a conventional process. With part of the free water having been lost during the ultrahigh frequency treatment, the drying is more rapid, in particular due to the migration of water from the wetter internal zones towards the peripheral zones whose water content is slightly lower. The resulting homogeneity of the water content thus enhances the removal of water by capillarity.

The manner in which the invention may be implemented and the resulting advantages will emerge more clearly from the exemplary of embodiments which follow.

EXAMPLE 1

The aerial parts (stem+leaves) of a non-flowered fresh passion flower (Pasiflora incarnata) are removed in a known manner.

Immediately after harvesting, the flavones contained in this plant are assayed by the conventional method using aluminium chloride and by determination of the optical density (OD) in the visible region using a spectrophotometer. It is thus determined that the freshly harvested plant contains about 78% of free water relative to the weight of the stems and leaves analysed and comprises 3.35% of flavones.

EXAMPLE 2

Stems and leaves are removed from the same batch as in Example 1, and this mixture is allowed to dry in open air for fifteen days at 22° C. in an atmosphere of 60% relative humidity, until all the free water is removed and 8.5% of residual water is obtained.

The mixture obtained is ground using a disk or a hammer mill. A grey-green coloured powder is obtained.

The flavones are assayed under the same conditions as in Example 1. 1.80% of flavones are obtained.

EXAMPLE 3

Passion flower stems and leaves from the same batch as in Example 1 were stored for three days at 22° C. in a relative humidity of 60%. The amount of free water decreased by 78% to 55–57%.

This material is then immersed in water at 22° C. for four minutes. The plant is removed, shaken in order to remove excess superficial water and then these plants are placed in a supporting tray so as to obtain a nearly uniform layer. Thereafter, the covered tray is introduced into a microwave oven equipped with two magnetrons so as to obtain a temperature close to 85° C. in the centre of the layer. This temperature is measured using a heat probe.

Immediately this temperature of 85° C. is obtained, which is suitable for the enzymes (cellulase and the like) to be destroyed, the oven is stopped, the tray is taken out, and the contents are spread out and dried in open air.

The residual water contained in these plants is 8.5%.

As in Example 2, the mixture is ground in a disk mill. A grey-green coloured powder is obtained whose flavones are assayed acid as previously described. 3.35% of flavones are obtained, that is to say exactly the same amount of flavones is preserved as that contained in the freshly harvested plant.

EXAMPLE 4

Example 3 is repeated but omitting the rehydration phase.

A grey-green coloured powder is also obtained comprising 2.02% of flavones (against 3.35%).

EXAMPLE 5

Example 3 is repeated on ash leaves (Fraxinus excelsior). Residual water (bound water) is 9%.

The flavones, measured as previously described, are 3%, that is to say of the same percentage as in the freshly harvested ash leaves.

EXAMPLE 6

Example 5 is repeated but omitting the rehydration stage. A substantial reduction in the level of flavones is obtained.

EXAMPLE 7

Example 5 is repeated but omitting the treatment according to the invention, that is to say omitting the rehydration phase and the ultrahigh frequency treatment but pursuing the natural drying at 22° C., 60% RH, until 9% residual water is obtained. 1.40% of flavones are thus obtained.

EXAMPLE 8

Example 1 is repeated using loosestrife roots (Lythrum salicaria) (and more specifically the rhizomatous strain).

These freshly harvested roots have 6% of water-soluble tannins.

When these roots are air-dried in a conventional manner, the proportion of water-soluble tannins decreases to 3.2%.

When these roots are subjected to the same treatment under the same conditions as in Example 3, 5.8% of water-soluble tannins is obtained.

EXAMPLE 9

Example 3 is repeated on sage leaves containing 8.5% of residual water. The treated leaves have a flavone content of 1.62%.

If the characteristic phase of rehydration is omitted, the water content remains the same but that of flavones drops to 1.05%. If the microwave treatment is also omitted, this flavone content decreases to 0.74%.

EXAMPLE 10

Example 3 is repeated on tarragon leaves containing 8.5% of water. The treated leaves have a flavone content of 4.30%.

If the rehydration phase is omitted, this content decreases to 2.11% and if in addition the microwave treatment is omitted, this content drops to 1.60%.

The plants treated in this manner may therefore be thus preserved with all their therapeutic, organoleptic or other properties for several months.

The process according to the invention makes it possible to obtain an optimal stabilisation of dried plants having similar properties to those of the initial fresh plants, while preserving their active ingredients, their taste and their odour.

The process according to the invention makes it possible to recover, in an economic manner, most of the desired and optimal properties of the plants without having to worry about treating them immediately after harvesting which, as is known, poses problems and considerably increases costs.

Thus, this process may be successfully used for treating plants having multiple uses such as for food, aromatic, condimental, cosmetic, medicinal or pharmaceutical use.

What is claimed is:

1. A process for stabilizing plants containing enzymes and therapeutic active ingredients that includes the steps of providing harvested plants of one variety containing not less than two-thirds of the plants' original water content at the time of harvest, said plants further containing enzymes having a lower denaturation temperature than that of the therapeutic active ingredient, determining the denaturation temperature of said enzymes, rehydrating the harvested plants at ambient temperature to restore the plants' water content to about 95% of that at the time of harvest, exposing the rehydrated plants to ultra high frequency radiation, monitoring the temperature of said plants during the radiation step, immediately terminating the radiation exposure when said predetermined denaturation temperature of said enzymes has been reached, and recovering at least 90% of the therapeutic active ingredients contained in the plants at the time of harvest.

2. The method of claim 1 that includes the further step of simultaneously exposing the rehydrated harvested plants to infrared radiation while said plants are being exposed to ultra high frequency radiation to more rapidly heat the plants to about the denaturation temperature of said plant enzymes.

3. The method of claim 1 wherein said harvested plants are treated with ultra high frequency radiation in a range of between 2400 to 2500 MHz.

4. The method of claim 1 that includes the further step of air drying said plants after said plants have been treated with ultra high frequency radiation.

5. The method of claim 1 wherein the harvested plants are rehydrated by immersing said plants in water at room temperature and further including the step of draining excessive water from said rehydrated plants prior to exposing the plants with ultra high frequency radiation.

* * * * *